(12) United States Patent
Jones et al.

(10) Patent No.: US 8,012,489 B2
(45) Date of Patent: Sep. 6, 2011

(54) RECOMBINANT VESICULAR STOMATITIS VIRUS VACCINES FOR VIRAL HEMORRHAGIC FEVERS

(76) Inventors: Steven Jones, Manitoba (CA); Heinz Feldmann, Hamilton, MT (US); Ute Stroeher, Manitoba (CA)

( * ) Notice: Subject to any disclaimer, the term of this patent is extended or adjusted under 35 U.S.C. 154(b) by 0 days.

(21) Appl. No.: 10/522,134

(22) PCT Filed: Jul. 28, 2003

(86) PCT No.: PCT/CA03/01125

§ 371 (c)(1),
(2), (4) Date: Aug. 29, 2005

(87) PCT Pub. No.: WO2004/011488

PCT Pub. Date: Feb. 5, 2004

(65) Prior Publication Data

US 2006/0193872 A1    Aug. 31, 2006

Related U.S. Application Data

(60) Provisional application No. 60/398,552, filed on Jul. 26, 2002, now abandoned.

(51) Int. Cl.
*A61K 39/12* (2006.01)
*C12Q 1/70* (2006.01)
(52) U.S. Cl. .................. 424/199.1; 424/204.1; 435/5
(58) Field of Classification Search .................. None
See application file for complete search history.

(56) References Cited

OTHER PUBLICATIONS

Kahn et al., Replication-Competent or Attenuated, Nonpropagating Vesicular Stomatitis Viruses Expressing Respiratory Syncytial Virus (RSV) Antigens Protect Mice Against RSV Challenge, Journal of Virology, Nov. 2001, vol. 75, No. 22, p. 11079-11087.*
Takada et al., A system for functional analysis of Ebola virus glycoprotein, Proceedings of the National Academy of Sciences of the United States of America, Dec. 1997, vol. 94. pp. 14764-14769.*
Schnell et al., Construction of a Novel Virus That Targets HIV-1-Infected Cells and Controls HIV-1 Infection, Cell, Sep. 1997, vol. 90, p. 849-857.*
Pushko et al., Individual and Bivalent Vaccines Based on Alphavirus Replicons Protect Guinea Pigs Against Infection with Lassa and Ebola Viruses, Journal of Virology, Dec. 2001, vol. 75. No. 23, pp. 11677-11685.*
Roberts et al., Attenuated Vesicular Stomatitis Viruses as Vaccine Vectors, Journal of Virology, May 1999, vol. 73, No. 5, pp. 3723-3732. See IDS 2$^{nd}$ reference.*
Pushko et al., Recombinant RNA replicons derived from attenuated Venezuelan equine encephalitis virus protect guinea pigs and mice from Ebola hemorrhagic fever virus, Vaccine, Aug. 2000, vol. 19. No. 1, pp. 142-153.*
Ito et al. Mutational Analysis of the Putative Fusion Domain of Ebola Virus Glycoprotein, Journal of Virology, Oct. 1999, vol. 73, No. 10, pp. 8907-8912.*
Takada et al. Proc. Natl. Acad. Sci. USA, Dec. 1997, vol. 94, pp. 14764-14769.*
Yang et al. Nature Medicine, Aug. 2000, vol. 6, No. 8, pp. 886-889.*
Vanderzanden et al. Virology, 1998, vol. 246, pp. 134-144.*
Takada et al., J. Virology, 2003, 77(2):1069-1074.*
Mahomadzadeh et al., Nature Reviews, 2007, 7:556-567.*
Haglund, Karl et al "High-level primary CD8[+] T-cell response to human immunodeficiency virus type 1 Gag and Env generated by vaccination with recombinant vesicular stomatitis viruses" Journal of Virology, vol. 76, No. 6, Mar. 2002; pp. 2730-2739 XP002266674.
Roberts, Anjeanette et al "Attenuated vesicular stomatitis viruses as vaccine vectors" Journal of Virology vol. 73, No. 5, May 1999, pp. 3723-3732 XP002266675.
Schnell, Matthias et al "Foreign glycoproteins expressed from recombinant vesicular stomatitis viruses are incorporated efficiently into virus particles", Proceedings of the National Academy of Sciences (USA), vol. 93, Oct. 1996 pp. 11359-11365 XP 002100328.
Ito, Hiroshi et al "Ebola virus glycoprotein: Proteolytic processing, acylation, cell tropism, and detection of neutralizing antibodies" Journal of Virology vol. 75, No. 3 Feb. 2001 pp. 1576-1580 XP002266671.
Trirawatanapong, Thaweesak et al "Mapping of a Region of Dengue Virus Type 2 Glycoprotein Required for Binding by a Neutralizing Monoclonal Antibody", Gene vol. 116 No. 2, 1992 pp. 139-150 XP000882966.
Wool-Lews Rouven J. et al "Characterization of Ebola Virus Entry by Using Pseudotyped Viruses: Identification of Receptor-Deficient Cell Lines" Journal of Virology vol. 72, No. 4 Apr. 1998 pp. 3155-3160 XP001036916.
Replication-Competent or Attenuated, Nonpropagating Vesicular Stomatitis Viruses Expressing Respiratory Syncytial Virus (RSV) Antigens Protect Mice against RSV Challenge; Jeffrey S. Kahn. et al.; Journal of Virology, Nov. 2001, p. 11079-11087; vol. 75, No. 22.
Development of a Preventive Vaccine for Ebola Virus Infection in Primates; Nancy J. Sullivan et al.; Letters to Nature, 2000 Macmillan Magazines Ltd., Nature/vol. 408/Nov. 30, 2000/www.nature.com, pp. 605-609.
DNA Vaccines Expressing either the GP or NP Genes of Ebola Virus Protect Mice from lethal Challenge; Lorna Vanderzanden; Virology Division, United States Army Medical Research Institute of Infectious Diseases, Ft. Detrick, Maryland 21702-5011: and PowderJect Vaccines, Inc. Madison Wisconsin 53711; Virology 246, 134-144 (1998) Article No. VY989176, pp. 134-144.
Vaccination with a Recombinant Vesicular Stomatitis Virus Expressing an Influenza Virus Hemagglutinin Provides Complete Protection from Influenza Virus Challenge; Anjeanette Roberts et al.; Journal of Virology, Jun. 1998, p. 4704-4711; American Society for Microbiology; vol. 72, No. 6.
Glycoprotein Exchange Vectors Based on Vesicular Stomatitis Virus Allow Effective Boosting and Generation of Neutralizing Antibodies to a Primary Isolate of Human Immunodeficiency Virus Type 1; Nina F. Rose et al. Journal of Virology, Dec. 2000, p. 10903-10910, American Society for Microbiology; vol. 74, No. 23.
High-Efficiency Incorporation of Functional Influenza Virus Glycoproteins into Recombinant Vesicular Stomatitis Viruses; Evelyne Kretzschmar et. al; Journal of Virology, Aug. 1997, p. 5982-5989, American Society for Microbiology, vol. 71, No. 8.
Towards a Vaccine Against Ebola Virus; Thomas W Geisbert et. al.; ISSN 1476-0584; Expert Rev. Vaccines 2(6), 777-789 (2003).
Identification of the Ebola Virus Glycoprotein as the Main Viral Determinant of Vascular Cell Cytotoxicity and Injury; Zhi_Tong Yang et al. , 2000 Nature America Inc. http://medicine.nature.com, vol. 6, No. 8, Aug. 2000, p. 886-889.

* cited by examiner

*Primary Examiner* — Stacy B Chen
(74) *Attorney, Agent, or Firm* — Michael R. Williams

(57) ABSTRACT

Recombinant VSV viral particles and the use thereof as vaccines for immunization are described.

6 Claims, 8 Drawing Sheets

Ebola Virus load in blood of immunized mice after Challenge

*x-axis:* days post infection
*y-axis:* TCID 50, Log base 10

Legend: VSV wt, VSV dG Ebola GP

Figure 8

RECOMBINANT VESICULAR STOMATITIS VIRUS VACCINES FOR VIRAL HEMORRHAGIC FEVERS

The application is a national phase filing of PCT CA03/01125, filed on Jul. 28, 2003 which claims the benefit of U.S. Provisional Patent Application Ser. No. 60/398,552, filed Jul. 26, 2002, now abandoned.

FIELD OF THE INVENTION

The present invention relates generally to the field of protective immune responses and recombinant viruses.

BACKGROUND OF THE INVENTION

Vesicular Stomatitis Virus (VSV) is a non-segmented negative-stranded RNA virus and belongs to the family Rhabdoviridae, genus *Vesiculovirus*. Its simple structure and rapid high-titered growth in mammalian and many other cell types has made it a preferential tool for molecular and cell biologists in the past 30 years. This was even strengthened with the establishment of the reverse genetics system for VSV (Schnell et al., 1996).

Viral Hemorrhagic Fever (VHF) viruses are prototypes of emerging/re-emerging pathogens. Infections are serious public health concerns not just in endemic, developing countries, but also in many non-endemic developed countries. Some of them represent a threat to the world's population and thus are listed on the category A list for bioterrorism agents. The high level of biological containment needed for their manipulation has impeded studies on viruses, such as Lassa virus, Marburg and Ebola viruses, in the past. Although these viruses can be grown in tissue culture, virus propagation is usually slow and titres are low compared with other viral pathogens.

While there are no worldwide licensed vaccines for the containment level IV viruses there has been a recent report that non-human primates were protected from Ebola infection by a DNA/adenovirus immunization (Sullivan et al., 2000). This vaccine strategy required several injections of naked DNA to both the glycoprotein (GP) and nucleoprotein (NP) of Ebola virus followed by injection of adenovirus expressing the gene for Ebola GP. However, the non-human primate protective vaccine required multiple doses of naked DNA and adenovirus boost to achieve protection and in Ebola, virus dose used to challenge the monkeys was only 6 plaque-forming units, which is very low. In general, the use of this vaccine to rapidly respond to outbreaks or bio-terrorist events is limited because it requires 8 weeks just to complete the immunization schedule.

Reverse genetics systems, such as the VSV (Schnell et al., 1996), may offer a chance to overcome some of the limitations and may actually be useful to study early steps of replication such as virus entry in the context of a viral particle. Different pseudotype systems have already been used to study the role of the Ebola virus glycoprotein in cell entry (Takada et al., 1997; Wool-Lewis, 1998; Yang et al., 2000). However, the use of pseudotype particles is limited to a single step infection and, thus, remains artificial. Recombinant viruses would be more realistic and powerful to study the role during replication in vitro and in vivo. The capability of the VSV genome to tolerate additional transcription units/genes makes this system suitable for high-level expression of foreign proteins. It is relatively uncomplicated in handling and, in general, virological approaches are easily applicable.

The goal of our study was to produce recombinant VSV particles expressing transmembrane and soluble glycoproteins derived from high containment viruses with the idea to study their role in virus replication, viral pathogenesis and induction of the host immune response. Here we describe the generation of several recombinant VSV particles and the characterization of their biological phenotype.

SUMMARY OF THE INVENTION

According to a first aspect of the invention, there is provided a recombinant vesicular stomatitis virus (VSV) particle comprising a nucleic acid molecule encoding a foreign glycoprotein inserted into the viral genome.

According to a second aspect of the invention, there is provided a nucleic acid molecule comprising recombinant vesicular stomatitis virus genome and a nucleic acid molecule encoding a foreign glycoprotein.

According to a third aspect of the invention, there is provided a method of eliciting an immune response in an individual comprising:
 administering to an individual a recombinant vesicular stomatitis virus (VSV) particle comprising a nucleic acid molecule encoding a foreign glycoprotein inserted into the viral genome.

According to a fourth aspect of the invention, there is provided a method of preparing a pharmaceutical composition for passive immunization of an individual in need of immunization comprising:
 administering to an animal a recombinant vesicular stomatitis virus (VSV) particle comprising a nucleic acid molecule encoding a foreign glycoprotein inserted into the viral genome;
 Harvesting antibodies from said animal; and
 mixing said antibodies with a suitable excipient or carrier, thereby forming a pharmaceutical composition.

BRIEF DESCRIPTION OF THE DRAWINGS

Figure 5:
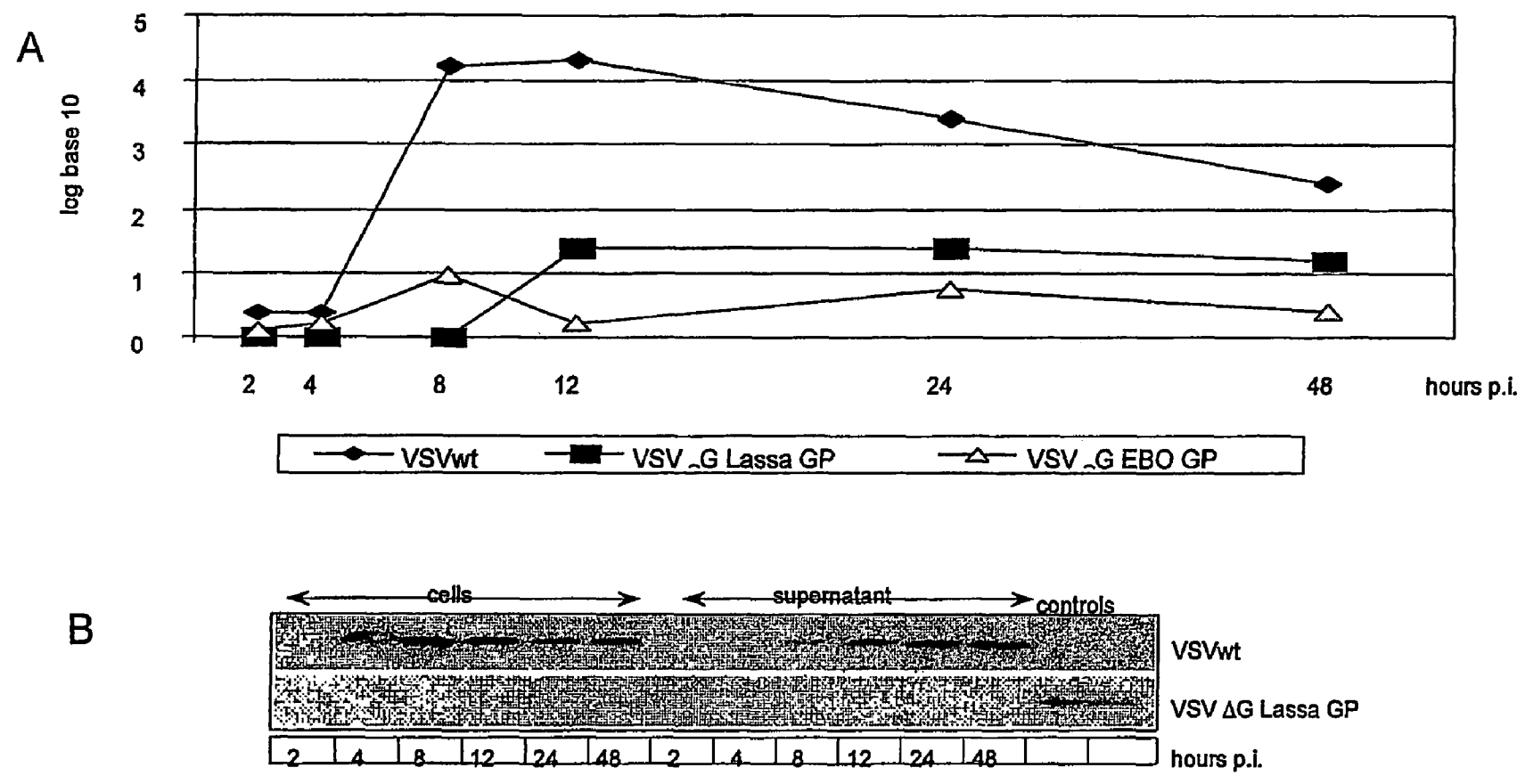

FIG. 5—Cell tropism: Jurkat cells were infected with VSVwt, VSV G Lassa G or VSV G Ebola GP at a MOI of 10. (A) Virus titres for the indicated time points were measured in Vero E6 cells by determining the tissue culture-infective dose (TCID)$_{50}$/ml. (B) At the indicated times cells and supernatants were harvested and virus growth was demonstrated by western blotting using a rabbit serum raised against VSV nucleoprotein (N).

FIG. 6—A schematic diagram of the normal VSV genome (A), the VSVΔG::EBOVGP (B, replacement of the VSV glycoprotein) and the VSV::EBOVsGP (C, normal VSV G plus Ebola secretory glycoprotein.

FIG. 8—Ebola virus titres in the blood of mice infected with 6000 LD$_{50}$ of mouse adapted Ebola virus. Ebola virus TCID$_{50}$ in blood samples from mice challenged with 6000 LD$_{50}$ of Mouse Adapted Ebola Zaire Mayinga. The TCID$_{50}$ of 2.3 (log$_{10}$) was the lower limit of detection in this assay. At no time was live Ebola virus isolated from the immunized mice. At day 6 all shame immunized (VSVwt) mice were very sick and all died by day 7. Mice were immunized with 1×10$^5$ pfu of either VSVwt or EbolaGP intraperitoneal injection.

DESCRIPTION OF THE PREFERRED EMBODIMENTS

Figure 1:
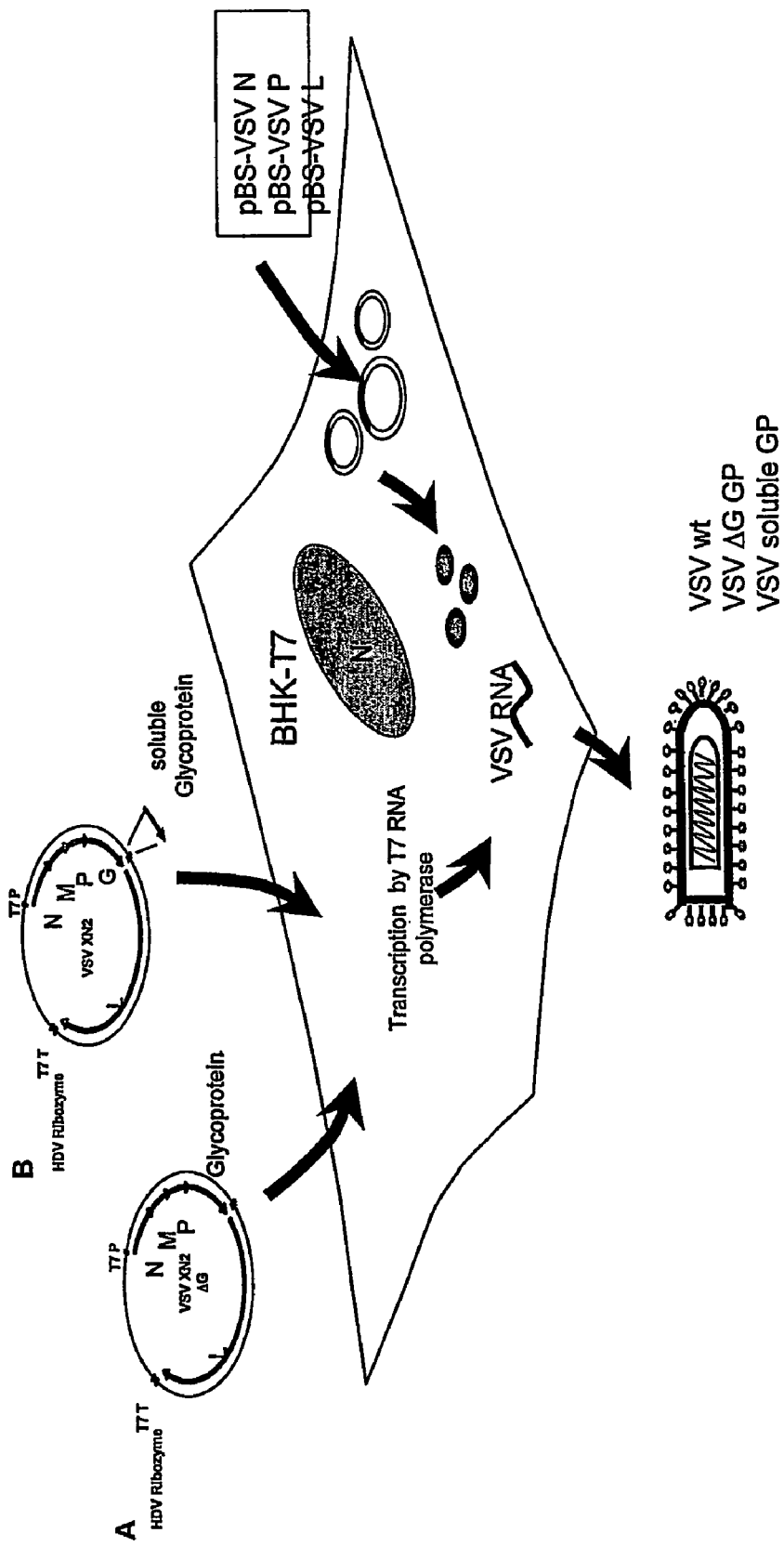
FIG. 1—Reverse genetic system for VSV. Schematic diagram of VSV rescue. Baby hamster kidney cells constitutively expressing the bacteriophage T7 polymerase (BHK-T7) cells were transfected with a plasmid for the expression of VSV cRNA synthesis, controlled by T7 RNA polymerase promoter and HDV ribozyme and supporter plasmids, encoding the proteins of the RNP.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Figure 6:
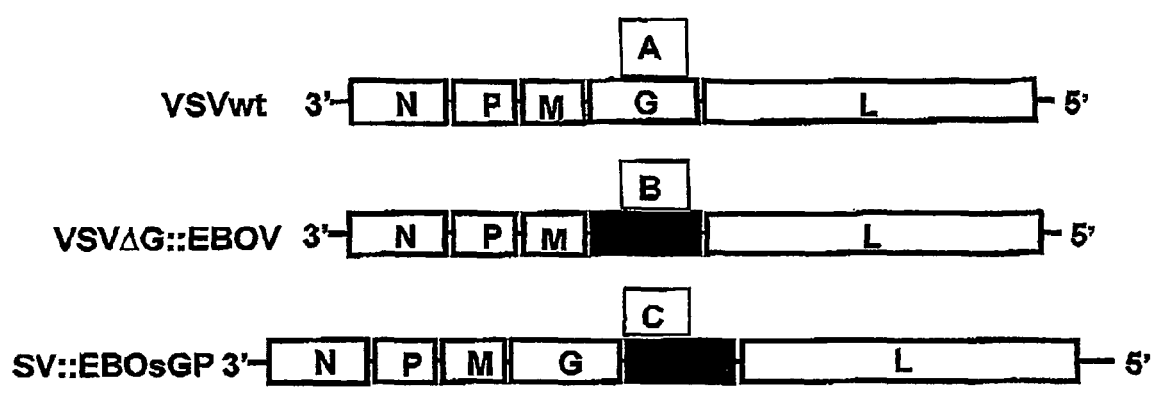

Described herein are recombinant vesicular stomatitis viruses (VSV) and recombinant VSV particles expressing foreign glycoproteins, for example, viral glycoproteins, exemplary examples of which are shown in FIG. 6. Also described is the use of the recombinant VSV particles to induce an immune response in an animal in need thereof.

In some embodiments, the foreign glycoprotein is a VHF glycoprotein or an immunogenic fragment thereof.

In some embodiments, the recombinant VSV may express the native VSV glycoprotein and have additional genes coding for foreign glycoprotein genes. These viruses have the host range of VSV but express the foreign glycoprotein genes during replication. These will have the uses as the glycoprotein replacement viruses.

The VHF glycoprotein may be, for example, but by no means limited to, the glycoprotein from Lassa virus, Marburg virus, Ebola virus, Crimean-Congo HF virus, Dengue virus, Nipah virus, Hendra virus, Machupo virus, Junin virus, Guanarito virus and Sabia virus. As will be appreciated by one of skill in the art, any enveloped virus with trans-membrane glycoproteins, which are determinants of immunity, may be used in this system. In other embodiments, immunogenic fragments of these glycoproteins may be used, as may fusion proteins including immunogenic fragments or epitopes of the glycoprotein of interest. As will be appreciated by one of skill in the art, there are numerous algorithms and/or computer programs available for predicting potentially immunogenic fragments and epitopes.

In some embodiments, the recombinant VSV may include nucleic acid molecules encoding genetic adjuvant sequences for eliciting a specific immune response pattern. The genetic adjuvants may be, for example, but by no means limited to, IL-2, IL-4, GM-CSF or costimulatory molecules CD80 and CD86.

In some embodiments, the gene order in the full length VSV genome clone may be altered such that the first gene will code for the glycoprotein rather than the nucleoprotein. This will have two effects: the virus will be further attenuated and more glycoprotein will be made, thereby increasing the efficacy of the vaccine.

Furthermore, in other embodiments, a foreign viral nucleoprotein is inserted along with the glycoprotein gene, thereby making a multivalent recombinant viral particle.

As will be apparent to one of skill in the art, only the foreign glycoprotein will be expressed on the surface of the recombinant VSV particle, and is thus presented to the host immune system. Thus, the recombinant VSV particle is an infectious system that simulates infection with the foreign virus and yet does not cause disease or the symptoms associated with the foreign virus. Furthermore, the immune response generated is protective regardless of the route of immunization. As will be apparent to one of skill in the art, only a single dose of the vaccine is required to elicit a protective immune response in the host, which may be a human. It is of note that the virus must be living to generate protection, as gamma-irradiated virus gave no protection.

In an exemplary example described below, the system simulates an infection with Ebola virus and yet has no adverse side effects. The recombinant VSV particle can protect against 2 million lethal doses of mouse-adapted Ebola virus and is protective following intra-nasal delivery, as discussed below.

As will be appreciated by one of skill in the art, the vectors containing the full length transmembrane GPs from Ebola Marburg and Lassa are viable because the foreign glycoproteins replaced the native VSV glycoprotein. Furthermore, it was believed that the GP of Ebola and Marburg were important virulence determinants and therefore disease symptoms were anticipated. The Ebola challenge was only done as an after thought when the mice survived infection with the recombinant VSV viruses.

It is of note that a recombinant VSV particle as described herein may be administered to an individual in need of such treatment orally, intravenously, intramuscularly, subcutaneously, intraperitoneally or intranasally. It is further of note that an individual in need of such treatment may be an individual at risk of infection by the foreign virus.

In yet other embodiments, the recombinant VSV particle is used to inoculate an animal for generating an immune response. In these embodiments, antibody-containing material is then harvested or purified and used as a post exposure therapy (passive immunity). As will be appreciated by one of skill in the art, the antibody containing material may be plasma, egg yolk, milk or the like.

The invention will now be described by way of examples; however, the invention is not limited to the examples.

EXAMPLE I

Plasmid Construction

A plasmid expressing the positive-strand RNA complement of the VSV genome with a site for foreign gene expression was described previously (Schnell, 1996). This plasmid contains the five VSV genes (nucleoprotein N, phosphoprotein P, matrixprotein M, glycoprotein G, and polymerase L) in order flanked by the bacteriophage T7 promoter, the VSV leader, the hepatitis delta virus (HDV) ribozyme, and the T7 terminator sequence. Between the G- and the L-gene a unique linker site (XhoI, NheI) is present, flanked by a transcriptional start and stop signal for the additional gene to be expressed. The genes encoding the soluble glycoproteins of Ebola virus (sGP) and Marburg virus (GP1) genes were cloned into the XhoI and NheI sites of the full length VSVXN2 vector (Schnell et al, 1996). The plasmids obtained were designated pVSVxn2/mbgGP1 and pVSVxn2/ebosGP respectively and have the foreign genes located between the VSV-G and L genes. The open reading frames encoding the transmembrane glycoproteins of Marburg, Ebola, and Lassa viruses were cloned into the XhoI and NheI sites of the modified full length VSVXN2ΔG vector lacking the VSV glycoprotein G. The resulting plasmids were called pVSVxn2 G/mbgGP, pVSVxn2 G/eboGP, and pVSVxn2 G/lvGPc.

EXAMPLE II

Transfection and Rescue of Recombinant VSV
(Recovery of Recombinant VSV

Recombinant VSVs were recovered using established methods. Baby hamster kidney cells constitutively expressing the bacteriophage T7 polymerase (BHK-T7) were grown to approximately 90% confluency in 6 cm dishes. The cells were then transfected in BSL2 with the support plasmids encoding the viral ribonucleoprotein (RNP) constituents, 0.5 µg PBS-N, 1.25 µg PBS-P, 0.25 µg PBS-L, and 2 µg of the plasmid encoding one of the above-described five recombinant genomic clones. Transfections were performed with Lipofectamine 2000 (Invitrogen), according to manufacturer's instructions. Since biosafety classification of these recombinant viruses had not been done at this time, we transferred the transfected cells immediately into BSL4. After 48 h at 37° C., supernatants were blind passaged onto VeroE6 cells (80-90% confluent). Subsequently, the recombinant VSV viruses have been classified as Biological containment level 2 viruses and therefore are suitable for human vaccination studies. Recovery of infectious virus was confirmed by scanning VeroE6 monolayers for VSV cytopathic effect. Rescued recombinant VSV was passaged on veroe6 cells to obtain a virus stock. The virus stock was plaque-titrated on Vero E6 cells.

EXAMPLE III

Immunfluorescence Microscopy

VeroE6 cells grown on coverslips were infected with the recombinant VSV at an MOI of 1. Following virus adsorption for 45 minutes at 37° C., the inoculum was replaced by Dulbeccos modified essential medium (DMEM) containing 2% FCS. Cells were fixed 24 hours post infection with 4% paraformaldehyde in PBS overnight. After a change of paraformaldehyde, cells were removed from BSL4 and gamma-irradiated ($2 \times 10^6$ rad). After inactivation, cells were washed with PBS and permeabilized with 0.1% triton-×100 in PBS for 15 minutes. Subsequently, the cells were incubated for 1 hour at room temperature with an appropriate primary antibody (diluted in PBS). The samples were washed three times with PBS and incubated for another hour with either a Cy3- or FITC-conjugated secondary (anti-species) antibody. Following washing (3 times), coverslips were mounted with Supermount (Biogenex, Germany) and examined with a Zeiss microscope.

EXAMPLE IV

Electron Microscopy

Recombinant VSV were grown in VeroE6 cells and virions were recovered from culture supernatants by ultracentrifugation and fixed in a solution of 2% paraformaldehyde and 0.5% glutaraldehyde. Fixed viral suspensions were transferred to copper electron microscopy grids pre-coated with carbon. The coated grids were bag-sealed and removed from BSL4. For inactivation, the grids were gamma-irradiated with $2 \times 10^6$ rads using a cobalt source. Negative staining was performed with 2% phosphotungstic acid (ph 6.8) for 1 minute. Excess fluid was removed and grids were examined using a transmission electron microscope.

EXAMPLE V

Metabolic Labelling, Immunoprecipitation and Immunoblotting

VeroE6 cells (6 cm dish) were inoculated with the recombinant VSV at a MOI of 10 pfu/cell. The inoculum was replaced after 1 hour by DMEM containing 2% foetal bovine serum (FBS) (both from Gibco/BRL). When Jurkat cells (clone e6-1, a t-cell clone) were infected, a slightly modified version of the protocol described by Montel, et al. (1997) was used. Briefly, cells were infected for 1 h at a MOI of 10 pfu/cell at room temperature with gentle mixing every 10-20 min. DMEM containing 2% foetal bovine serum (FBS) was then added and culture continued for 1 h at 37° c. Cells were then washed 3 times in DMEM, resuspended at $10^6$ cells/ml in media containing 2% FBS, with 1 ml per well of a 12 well dish. For metabolic labelling experiments, cells were incubated for 24 h, washed with DMEM deficient in cysteine, pulse labelled for 30' in the same medium supplemented with 20 µCi/ml [$^{35}$S]-methionine/cysteine and chased for 240'. For cleavage inhibition studies the infected cells were incubated during starvation, pulse, and chase periods with the decanoylated peptidylchloromethylketone (decrvkr-cmk) at a concentration of 25 μm. labelled cells were lysed in co-immuniprecipitation (co-ip) buffer [1% nonidet p-40 (np-40), 0.4% sodium deoxycholate, 0.5% BSA, 5 mm EDTA, 100 mm NaCl, 20 mm Tris-HCl ph 7.6, 25 mm iodoacetamide, 1 mm pmsf] at 4° c. Immunprecipitation was performed using a protein-specific monoclonal antibody. Precipitated proteins were subjected to 10% SDS-PAGE under reducing conditions and visualized by fluorography. For immunoblot analysis, cells were washed 24 hours post infection with PBS and lysed in SDS gel loading buffer. Proteins were resolved by SDS-PAGE (10%) and transferred to PVDF membranes. Expression of the foreign protein was detected using appropriate antibodies.

EXAMPLE VI

Growth Characteristics of the Recombinant VSV

VeroE6 cells were cultured to cell density of $10^6$ per well of a 12 well dish and infected with the different recombinant VSV at a MOI of 10 pfu/cell. Cells were then washed 3 times in DMEM and 1 ml fresh media containing 2% FBS was added. Cultures (cells and supernatants) were harvested at the time points indicated and centrifuged at 3000 g for 5 min at 4° c. The supernatants were stored at −80° c. Titration was performed by defining the 'tissue culture infectious dose' (TCID) 50. For this the supernatants were diluted 10-fold and the dilutions were used to infect VeroE6 cells in 96-wells (five wells for each dilution). The cultures were scored periodically for cytopathogenic effects (c.p.e.) over a period of 7 days. The end-point virus titres for culture supernatants were calculated using the method of Reed and Muench (1938). Viral titers are expressed as log 10 of the 50 percent titration endpoint for infectivity as calculated by the method of Spearman Karber.

EXAMPLE VII

Mouse Data

Figure 7:
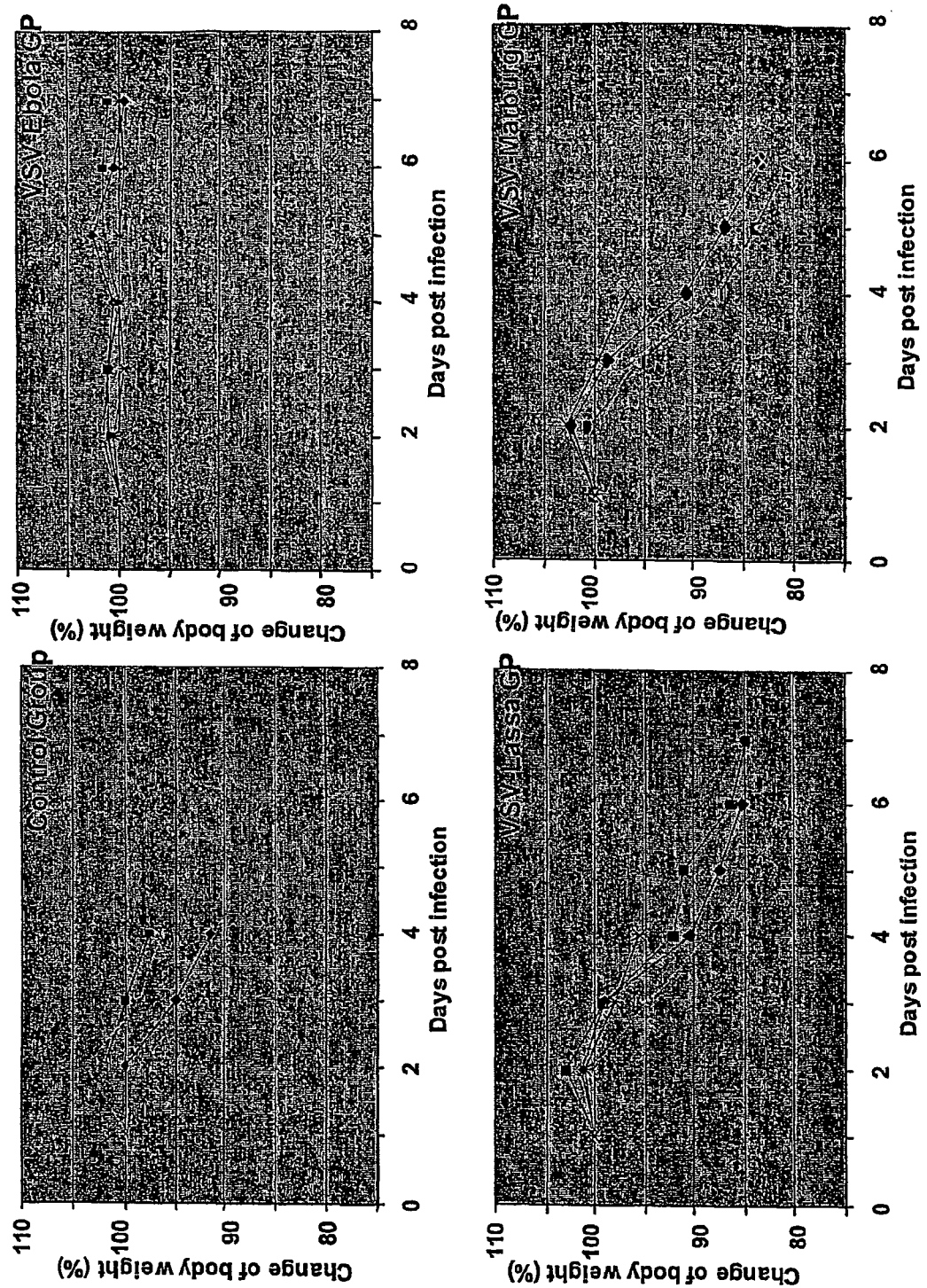
FIG. 7—Clinical signs of disease we assessed including percentage weight change after challenge with 6000 LD$_{50}$ Mouse adapted Ebola virus. Percentage body weight change of mice immunized on day 0 and 21 (intraperitoneal route) with 1×10$^5$ pfu of VSV Lassa GP, VSV-EbolaGP, VSV Marburg GP or Naïve controls and then challenged with 6000 LD$_{50}$ Mouse Adapted Ebola Mayinga (intraperitoneal route). All mice in the VSV Lassa GP, VSV Marburg GP and Naïve Control groups died by day 8. All mice immunized with VSV-Ebola GP survived challenge to day 28 and showed no loss in body weight.

Groups of 5 female mice were immunized with $10^5$ plaque-forming units (p.f.u.) of VSVΔG::EBOVGP (EbolaGP), VSVΔG::MBGVGP, VSVΔG::LassaVGP or wild-type VSV (VSVwt). Two doses of vaccine were given on day 0 and day 28. On each occasion, the vaccine was administered by the intra-peritoneal route (i.p.). 28 days after the boosting dose, the mice were challenged with 6000 $LD_{50}$ of mouse adapted Ebola virus. The mice receiving EbolaGP were completely protected from Ebola virus infection whereas all of the mice in the other groups rapidly succumbed to the infection (Table 1). The measurement of clinical signs is a rather more sensitive assay of protection than simply looking for survival. As part of the clinical observation, mouse weights were recorded and the individual percentage change after challenge was calculated (FIG. 7). The results demonstrated that there was a clear specific protective effect of immunization with the EbolaGP vaccine.

The next step was to try and protect mice after just a single dose of vaccine. The mice were again immunized with $10^5$ p.f.u. of either VSVwt or EbolaGP again i.p. on day 0. The mice were then challenged with mouse adapted Ebola virus 28 days after immunization. On this occasion, the immunized mice were challenged with between $2\times10^3$ and $2\times10^6$ p.f.u. of Ebola virus and the VSVwt control mice were challenged with $2\times10^2$ p.f.u. All of the control mice rapidly displayed symptoms and weight loss whereas all of the immunized mice remained healthy and without symptoms. Therefore, the EbolaGP vaccine protection is apparently independent of challenge dose (FIG. 8).

Figure 9:
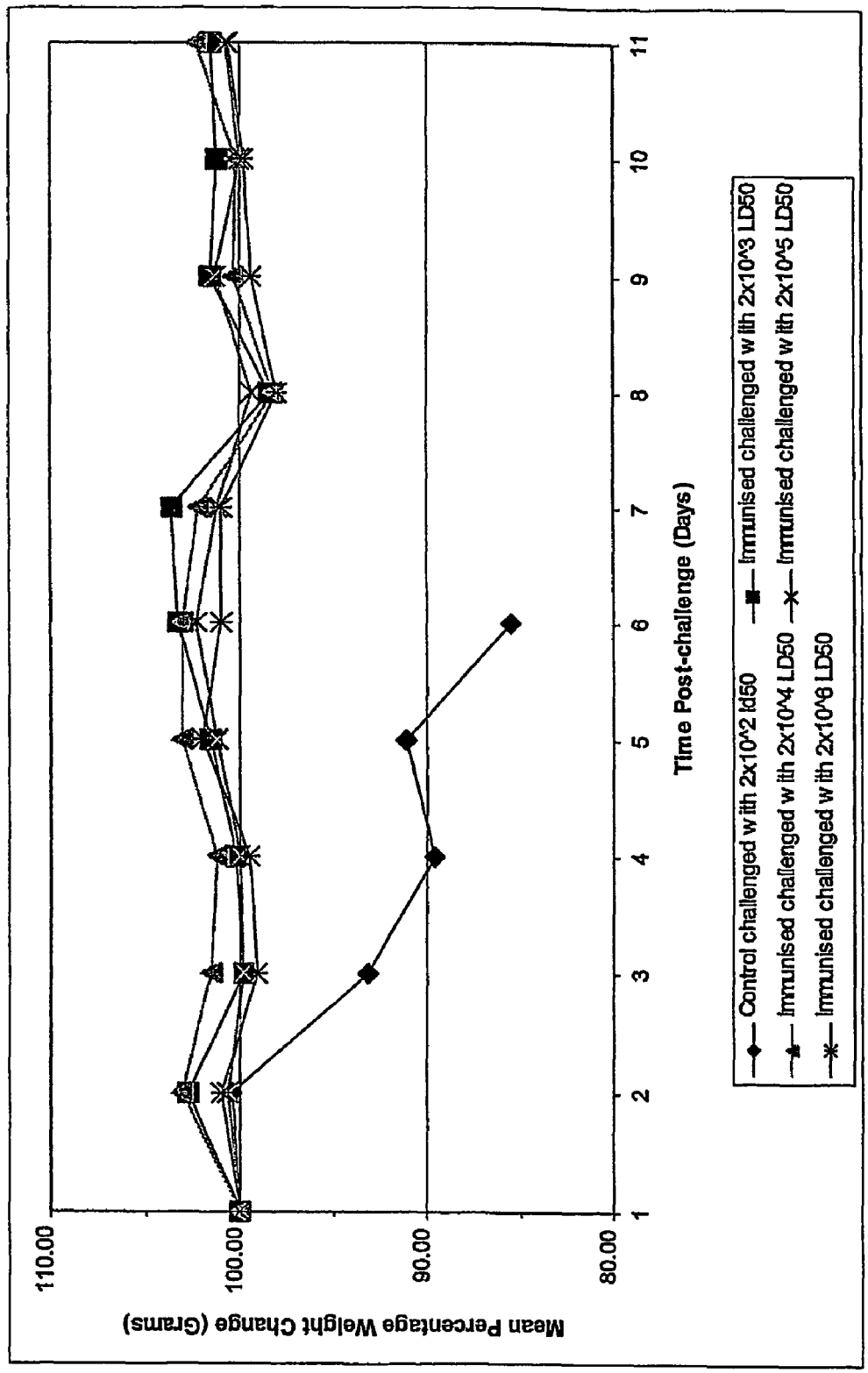
FIG. 9—The protection afforded by the EbolaGP vaccine is independent of the challenge dose. Mice were immunized with 1×10$^5$ pfu of either VSVwt (1 group n=6) or EbolaGP (4 groups n=6) by intraperitoneal injection once on day 0. On day 28 the animals were challenged with Mouse Adapted Ebola Zaire Mayinga in increasing doses 6000 LD$_{50}$ to 6 million LD$_{50}$. All the VSVwt control animals died by day 7 and all exhibited dramatic weight loss and clinical symptoms of viral hemorrhagic fever prior to death, these mice were challenged with 6000 LD$_{50}$. The EbolaGP mice were challenged with between 2×10$^3$ and 2×10$^6$ LD$_{50}$ and all survived without displaying any symptoms or losing weight.

We determined the Ebola viremia for 6 days after challenge in both VSVwt and EbolaGP immunized mice (FIG. 9). Three mice from the vaccine and wild type control groups were culled daily and blood and spleen removed for virus titre estimation ($TCID_{50}$). It was not possible to detect Ebola virus in the blood of mice immunized with the EbolaGP vaccine at any time. However, mice that received the VSVwt vaccine developed a viremia on day 3 post-infection and this viremia became progressively worse until the mice died by day 7.

All studies so far have been conducted using the i.p. route. This route is useful for experimental immunization but could not be used for human vaccination. Therefore, we investigated the effect of route of vaccination on protection and as shown in Table 2, protection is independent of immunization route. However, the vaccine must be viable at the time of immunization to afford protection as gamma irradiated vaccine failed to protect the mice from Ebola infection.

In summary, we have developed a vaccine that can protect mice from Ebola infection. This protection could not be defeated by increasing the challenge dose and was not affected by altering the route of immunization. Furthermore, it appears that the viremia is completely controlled in the immunized mice and this is demonstrated by the complete lack of clinical symptoms in these mice as well as by the $TCID_{50}$ data.

EXAMPLE VIII

Results & Discussion

The ability to genetically manipulate VSV has already led to a variety of new insights in the field of VSV research in regard to structure-function studies of viral genes, the analysis of promoter elements and other non-coding elements. In addition, the capability of the VSV genome to tolerate additional transcription units/genes or to exchange the glycoprotein gene by a foreign transmembrane glycoprotein makes this system useful for high-level expression purposes. Furthermore, recombinant VSVs were used as promising live virus vaccine candidates (Influenza A virus, HIV, BVDV). The potential role of recombinant VSVs as vaccines is supported by the facts that VSV and rVSVs grow to very high titers in many cell lines, that VSV elicits a strong cellular and humoral immune response in vivo, and that VSV infections of humans are rare and the symptoms, if at all, are mild.

Figure 2:
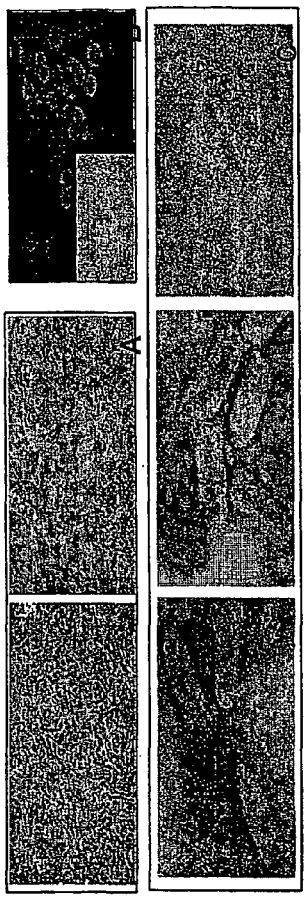
FIG. 2—VSV G MBG GP infection. (A) CPE of infected Vero E6 cells was shown by phase contrast microscopy 24 h post infection. (B) Immunfluorescence staining of infected Vero E6 cells with a MBG GP1 specific antibody. Electron micrographs showing VSV G MBG GP, VSVwt & VSV G Lassa GP.

In this study, we wanted to establish a system to express and study the function of soluble glycoproteins and transmembrane glycoproteins of viral hemorrhagic fever viruses. For this, we modified the full-length cDNA clone (pVSVxn2) by either replacing the VSV G gene with the glycoproteins of MBGv, EBOv and Lassa virus or inserting the genes which encode the EBOv sGP (Volchkov et al., 1995; Sanchez et al., 1996) and MBGV GP1, which is the large cleavage fragment released during tissue culture infection (Volchkov et al., 1998a, b), between the VSV G and L genes. These cDNAs were transfected into BHL-T7 cells and virus was rescued. The rescued viruses were designated VSV G MBG GP, VSV G EBO GP, VSV g Lassa G, VSV MBG GP1 and VSV EBO sGP, respectively. Electron microscopy studies (FIG. 2) of negatively contrasted recombinant viruses provided data that substitution of the VSV glycoprotein G has no impact on the morphology of the virions. Recombinant VSV, regardless of the inserted glycoprotein, showed typical bullet-shaped rhabdovirus particles and contained an electrodense bullet-shaped nucleocapsid. The nucleocapsid was bound by an envelope. The viral envelopes were coated with surface projections. The foreign proteins could completely substitute for VSV G in assembly and did not influence the particle structure formation.

Furthermore, processing of the foreign glycoproteins seems to occur in the same manner as in the authentic VHF virus systems. Using immunological and biochemistry methods, we confirmed the expression and proteolytic processing of the foreign viral glycoproteins. Immunofluorescence staining exemplarily shown for VSV G MBG GP infected VeroE6 cells using a GP specific antibody detects MBG GP on the surface of infected cells (FIG. 2B).

Figure 3:
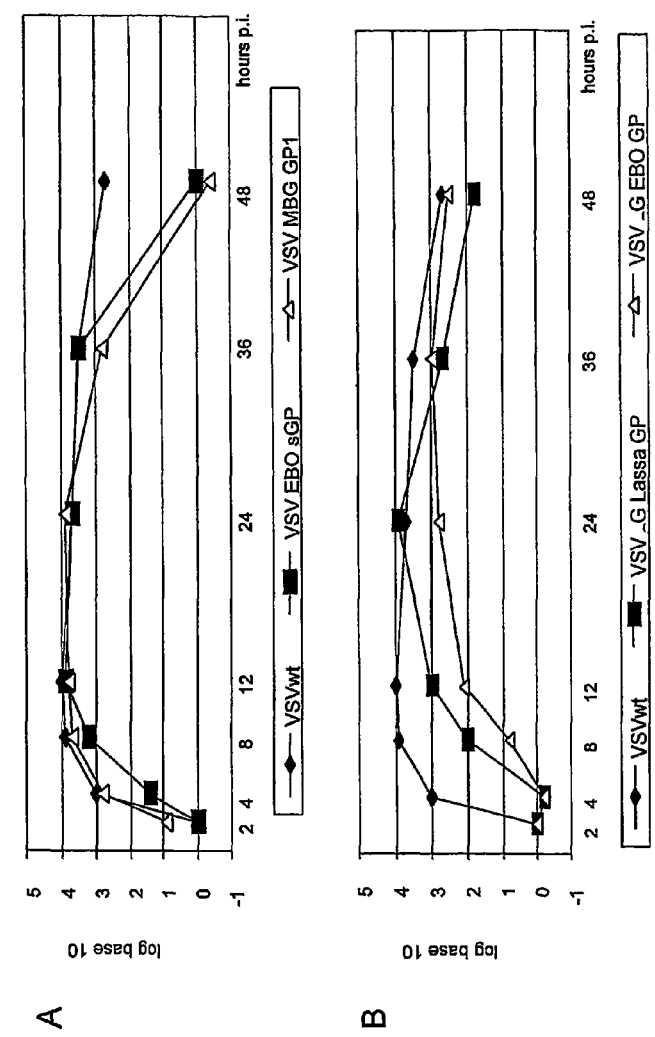
FIG. 3—Growth curves of recombinant VSV. Vero E6 cells were infected with A) VSVwt, VSV EBO sGP, MBG GP1 and B) with VSVwt, VSV G EBO GP and VSV G Lassa GP at a Multiplicity of Infection (MOI) of 10. Supernatants were collected at the indicated times and titred by defining the 'tissue culture infectious dose' $(TCID)_{50}$.
Figure 4:
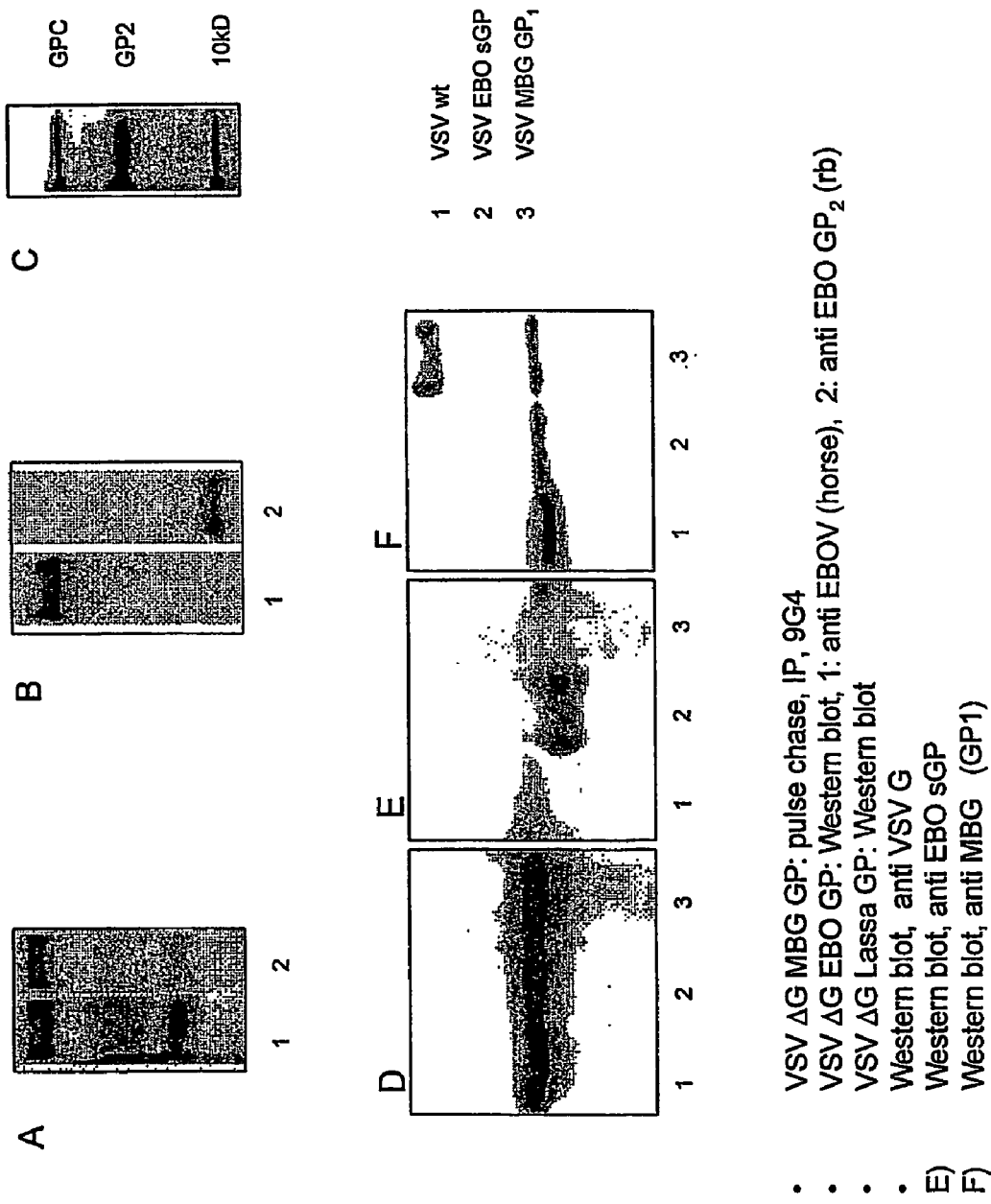
FIG. 4—Expression of glycoproteins expressed by recombinant VSV. VeroE6 cells were infected with the recombinant VSV at a MOI of 10. A) VSV G MBG GP: 24 hours post infection proteins were pulse labelled for 30 min with 20 µCi/ml $[^{35}S]$ cysteine and chased for 6 hours. GP-specific proteins were immunoprecipitated from cell lysates with mouse anti MBG GP immunoglobulins and analyzed on 10% SDS-PAGE under reducing conditions. The presence of the decrvkr (25 mm) (a cleavage inhibitor) during labelling and chase abolished cleavage of preGP (lane 2). B) VSV G EBO GP: 24 hours post infection cells were lysed and analyzed by western blotting with a GP1 specific Ab (lane 1) and GP2 specific Ab (lane 2). C) VSV G Lassa G: 24 hours post infection cells were lysed and analyzed by western blotting with a G2 specific Ab. D-F) VSVwt (lane 1), VSV EBO sGP (lane 2), VSV MBG GP1 (lane 3): 24 hours post infection cells were lysed and analyzed by western blotting with a VSV G specific Ab (D), an EBO sGP specific antibody, and a MBG GP1 specific antibody.

Proteolytic processing of the MBGV glycoprotein into the two cleavage fragments GP1 (160 kDa) and GP2 (38 kDa) is shown in FIG. 3A by immunoprecipitation with a MBG GP monoclonal Ab. The cleavage of VSV encoded MBG GP was significantly restricted when GP was expressed in the presence of the decanoylated peptidyl chloromethylketone decrvkr-cmk, a potent inhibitor of the subtilisin-like endoprotease furin. Expression and proteolytical processing of EBO GP and Lassa G were demonstrated by immunoblot analysis. The two cleavage fragments of the EBOV transmembrane glycoprotein GP1 (140 kDa) and GP2 (26 kDa) were detected with an anti GP serum, which recognizes GP1 (FIG. 3B, left lane), and a monospecific anti GP2 serum (FIG. 3B, right lane). Part C demonstrates the cleavage of the Lassa virus glycoprotein precursor (76 kDa) into G1 (not shown) and G2 (36 kDa). In this case, detection was performed with a specific antiserum raised against the carboxyl-terminus of G2. In addition to the precursor (not fully cleaved) and the G2 fragment, a so far unknown 10 kDa fragment was detected which needs further attention. Expression of the soluble glycoproteins by the recombinant VSV is shown in FIG. 3 part D-F. In addition to VSV G, which is expressed by VSVwt, VSV MBG GP1 and VSV EBO sGP infected cells (FIG. 3D lanes 1-3), EBO sGP (FIG. 3E lane 2) and MBG GP1 (FIG. 3F lane 3) are only detectable in cells infected with the respective recombinant virus as demonstrated here using monospecific Ab.

Replication of the recombinant viruses under single-step growth conditions was examined in Vero E6 cells infected at a MOI of 10 followed by incubation at 37° C. Supernatant fluid were harvested at various times, and the virus yields were measured by $TCID_{50}$.

FIG. 3 part B shows the growth kinetics for the recombinant viruses with a replacement of the VSV glycoprotein. Viral titres for VSVwt, VSV G Lassa GP or VSV G Ebola GP reached three to four logs greater than background levels. However, maximum titres were reached between 8 h and 12 h post infection for VSVwt, 24 h post infection for VSV G Lassa GP and 36 h post infection for VSV G Ebola GP. This indicated differences in replication for the recombinant viruses if the VSV glycoprotein is replaced by a foreign glycoprotein. The recombinant viruses, which contain additional transcription units, have similar growth kinetics compared to VSV wild type. FIG. 3 part A shows the growth curves for VSV Ebola sGP or VSV MBG GP1. Virus titres for VSVwt, VSV Ebola sGP or VSV MBG GP1 reached three to four logs greater than background levels, and maximum titres were reached between 8 h and 12 h post infection in all three cases indicating that the addition of genes does not affect the growth kinetics of the recombinant viruses.

Cell tropism studies revealed that the tropism of the recombinant viruses is, as expected, dependent on the transmembrane glycoprotein and not influenced by the additional soluble glycoproteins expressed from a separated transcription unit. Virus titres for VSVwt in Jurkat cells reached four logs greater than background levels between 8 h and 12 h post infection. However, VSV G Lassa GP and VSV G Ebola GP failed to infect and replicate in Jurkat cells. This indicated that the replacement of the VSV glycoprotein led to a change in cell tropism as expected from infection studies using Ebola and Lassa viruses which both do not set a productive infection of Jurkat cells. In order to confirm the results, immunoblots were performed. Cells were infected with VSVwt and VSV G Lassa G at a MOI of 10 pfu/cell. At time points indicated, cells and supernatants were harvested and analyzed by immunoblot using a rabbit serum raised against VSV N. VSVwt was detected earliest at four hours post infection intracellularly and eight hours post infection in the supernatant indicating release of virus particles. No replication was detectable for VSV G Lassa GP and VSV G EBO GP virus, which confirmed that these recombinant viruses are not able to productively infect Jurkat cells. The advantage of replication competent VSVs coding for foreign glycoproteins, beside their use in cell tropism studies in vitro, is the potential to use these viruses in in vivo studies, where multiple replication cycles are necessary. This includes for example the investigation of host range or organ tropism. Recombinant VSVs with altered (specified) cell tropism (organ tropism) might be even useful for cell specific gene delivery approaches.

Thus, these recombinant viruses represent an excellent system to study the role of the glycoproteins in cell tropism and pathogenesis in vivo and in vitro. Preliminary animal data further suggest that the recombinant viruses can be manipulated more safely than the donor VHF viruses.

Referring to Table 3, it is of note that the guinea pig is considered to be a more sensitive model for Ebola virus infection and consequently more difficult to protect. However, the data in Table 3 indicates that the vaccine is very potent and is capable of protecting at least two different species.

Referring to Table 4, this data shows that we have a single dose mucosal vaccine capable of protecting animals from challenge with 6 million virus particles. Obviously mucosal vaccines whether oral or intranasal are much easier to deliver than injected ones and could be more easily deployed in the event of a bioterrorist attack or outbreak of disease. The high level of protection achieved would indicate that protection could be achieved from a bioterrorist attack or accidental needle stick injury in a hospital treating patients.

Referring to Table 5, this data shows that we can achieve complete protection with immunization just 7 days prior to challenge and significant protection ($p<0.05$) when given 30 minutes after challenge indicating that there is scope for a post exposure vaccine therapy. Taken together, the two data sets demonstrate significant potential application in prevention of disease in outbreak situations and as a vaccine used in response to bioterrorist or biological weapon attack. The time to develop immunity following the administration of the EbolaGP vaccine is much short than that required for the vaccine described by (Sullivan et al, 2000)

Referring to Table 6, a single immunization resulted in protection lasting for at least 9 months with no apparent decrease in potency. Extrapolation of this data indicates that a single application of the vaccine would probably induce immunity in human populations lasting for several years.

Referring to Table 8, this result implies that it may be possible to use the instant vaccines to produce immune serum, poly- or mono-specific, for passive protection of humans infected with Ebola or other VHF agents for which we can make VSV recombinants.

The EbolaGP vaccine is currently being tested in non-human primates. This animal model is the most similar to human disease. Four animals will be immunized with EbolaGP $2\times10^7$ pfu. They will be challenged in 28 days with Ebola virus by im injection. During the period before challenge, the animals will be monitored for immune response and for pathology caused by the vaccine. We expect to see the development of protective immunity and no serious side effects in the monkeys. At challenge, we expect the four immunized animals to remain symptom free throughout the study and the control animal to die between days 5 and 10. The protection of primates and the safety of the vaccine will be demonstrated by this study.

While the preferred embodiments of the invention have been described above, it will be recognized and understood that various modifications may be made therein, and the appended claims are intended to cover all such modifications which may fall within the spirit and scope of the invention.

REFERENCES

Sullivan N J, Sanchez A, Rollin P E, Yang Z-Y, Nabel G J. 2000. Development of a preventative vaccine for Ebola virus infection in primates. Nature 408:605-609

Schnell M J, Buonocore L, Kretzschmar E, Johnson E, Rose J K. 1996. Foreign glycoproteins expressed from recombinant vesicular stomatitis viruses are incorporated efficiently into virus particles. Proc Natl Acad Sci USA 93: 11359-11365.

Takada A, Robison C, Goto H, Sanchez A, Murti K G, Whitt M A, Kawaoka Y. 1997. A system for functional analysis of Ebola virus glycoprotein. Proc Natl Acad Sci USA. 94(26): 14764-9.

Wool-Lewis R J, Bates P. 1998. Characterization of Ebola virus entry by using pseudotyped viruses: identification of receptor-deficient cell lines. J Virol. 72(4):3155-60.

Yang Z Y, Duckers H J, Sullivan N J, Sanchez A, Nabel E G, Nabel G J. 2000. Identification of the Ebola virus glycoprotein as the main viral determinant of vascular cell cytotoxicity and injury. Nat Med. 6(8):886-9.

Montel A H, Hommel-Berrey G, Brahmi Z. 1997. Fas-mediated cytotoxicity induces degradation of vesicular stomatitis virus RNA transcripts and reduces viral titer. Mol Immunol. 34(15):1055-66.

Volchkov V E, Becker S, Volchkova V A, Ternovoj V A, Kotov A N, Netesov S V, Klenk H D. 1995. GP mRNA of Ebola virus is edited by the Ebola virus polymerase and by T7 and vaccinia virus polymerases. Virology.214(2):421-30.

Sanchez A, Trappier S G, Mahy B W, Peters C J, Nichol S T. 1996. The virion glycoproteins of Ebola viruses are encoded in two reading frames and are expressed through transcriptional editing. Proc Natl Acad Sci USA. 93(8): 3602-7.

Volchkov V E, Volchkova V A, Slenczka W, Klenk H D, Feldmann H. 1998. Release of viral glycoproteins during Ebola virus infection. Virology. 245(1):110-9.

Volchkov V E, Feldmann H, Volchkova V A, Klenk H D. 1998. Processing of the Ebola virus glycoprotein by the proprotein convertase furin. Proc Natl Acad Sci USA. 95(10):5762-7

TABLE 1

Survival of immunized and control mice after challenge with $6000 LD_{50}$ mouse adapted Ebola virus

| Treatment | Survivors at day 28 | Mean time to death (days) |
|---|---|---|
| VSVwt | 0/5 | 5.6 |
| VSVΔG::MBGVGP | 0/5 | 6.6 |
| VSVΔG::LassaVGP | 0/5 | 7.0 |
| EbolaGP | 5/5 | N/A |

TABLE 2

| Treatment | Survivors at day 28 | Mean time to death (days) |
|---|---|---|
| Naïve controls | 0/4 | 7.4 |
| VSVwt intra-peritoneal | 0/5 | 5.5 |
| VSVwt intra-muscular | 0/5 | 5.0 |
| VSVwt sub-cutaneous | 0/5 | 5.2 |
| VSVwt intra-nasal | 0/5 | 5.8 |
| EbolaGP i.p. | 5/5 | N/A |
| EbolaGP i.m. | 5/5 | N/A |
| EbolaGP sc | 5/5 | N/A |
| EbolaGP in | 5/5 | N/A |
| gamma-irradiated EbolaGP ip | 0/5 | 7.0 |

TABLE 3

Duncan Hartley Guinea Pigs were completely protected from challenge with Guinea Pig Adapted Ebola Virus following intramuscular immunization with 200 μl of $1 \times 10^5$ pfu of EbolaGP. VSV wt and untreated control animals all died.

| | EbolaGP immunized | Naïve Control | VSV wild type Control | Percentage Survival to 28 |
|---|---|---|---|---|
| Days post infection | 0 | 0 | 100 | |
| Mean time to death (days) | 6 | 5.83 | — | |

TABLE 4

Complete protection of Balb/c mice challenged by intraperitoneal injection with between $6 \times 10^2$ and $6 \times 10^6$ $LD_{50}$'s of mouse adapted Ebola virus. Mice were immunized once with EbolaGP vaccine by either intranasal instillation, or injection intrapertoneal or intramuscular routes, 28 days before infection. The challenge dose was between $6 \times 10^2$ and $6 \times 10^6$ $LD_{50}$'s of mouse adapted Ebola virus. Mice immunized on two occasions (days 0 to 28) by oral gavage were protected from intraperitoneal challenge with $6 \times 10^3$ $LD_{50}$'s of mouse adapted Ebola virus. Percentage survival to 28 days post challenge. nt = not tested.

| Treatment | Immunization Route | Challenge Dose ($LD_{50}$'s) | | | | |
|---|---|---|---|---|---|---|
| | | $6 \times 10^6$ | $6 \times 10^5$ | $6 \times 10^4$ | $6 \times 10^3$ | $6 \times 10^2$ |
| EbolaGPp | IN | 100 | 100 | 100 | 100 | 100 |
| | IM | 100 | 100 | 100 | 100 | 100 |
| | IP | 100 | 100 | 100 | 100 | 100 |
| | Oral | nt | nt | nt | 100 | nt |
| VSV wt | IP | 0 | 0 | 0 | 0 | 0 |
| VSV wt | Oral | nt | nt | nt | 0 | nt |
| Naïve | None | nt | nt | nt | 0 | 0 |

TABLE 5

Specific, complete protection is afforded by a single intraperoitoneal immunization of mice 7 days before challenge and significant protection ($p < 0.05$) is provided by immunization 30 minutes after challenge. Furthermore, non-specific protection can be demonstrated in mice immunized with either EbolaGP or VSV wt up to 3 days post challenge. All animals were infected with $6 \times 10^3$ $LD_{50}$'s of mouse adapted Ebola virus. Percentage survival to 28 days post challenge.

|  | −28 | −21 | −14 | −7 | −3 | 0 | +1 | +2 | +3 |
|---|---|---|---|---|---|---|---|---|---|
| EbolaGP | 100 | 100 | 100 | 100 | 100 | 80 | 80 | 100 | 20 |
| VSVwt | 0 | 0 | 0 | 0 | 20 | 0 | 60 | 100 | 40 |
| Naïve | nt | nt | nt | nt | nt | nt | nt | nt | nt |

TABLE 6

Complete protection afforded by a single ip immunization with EbolaGP vaccine is long lasting. Percentage survival to 28 days post challenge.

| | Time of challenge (months post immunization) | | |
|---|---|---|---|
| | 3 months | 6 months | 9 months |
| Naïve | 0 | 0 | 0 |
| VSV wt | 0 | 0 | 0 |
| EbolaGP | 100 | 100 | 100 |

TABLE 7

Protection of mice is not dependent on cytotoxic t-cell responses.

| Treatment | Percentage survival at 28 days post challenge |
|---|---|
| CD4 depleted | 40 |
| CD8 depleted | 100 |
| Undepleted | 100 |

TABLE 8

Passive transfer of serum from mice immunized with the EbolaGP vaccine protects naïve mice from challenge with $6 \times 10^3$ $LD_{50}$'s of mouse adapted Ebola virus

| Treatment | Percentage survival | Mean Time to Death |
|---|---|---|
| Naïve serum | 0 | 5.8 |
| VSV wt immune serum | 0 | 6 |
| EbolaGP serum | 80 | 1 death at day 11 |

The invention claimed is:

1. A vaccine comprising:
   a live, replication-competent recombinant vesicular stomatitis virus (VSV) particle comprising a nucleic acid molecule encoding a viral hemorrhagic fever (VHF) glycoprotein selected from the group consisting of a glycoprotein from Lassa virus; a glycoprotein from Marburg virus; and a glycoprotein from Ebola virus, inserted into the viral genome wherein the foreign glycoprotein has replaced the native VSV glycoprotein and only the VHF glycoprotein is expressed on the surface of the recombinant VSV particle, wherein said recombinant VSV particle is infectious.

2. The vaccine according to claim 1 wherein the first gene of the recombinant VSV codes for the VHF glycoprotein.

3. A method of vaccinating an individual comprising:
   administering to an individual a live, replication competent recombinant vesicular stomatitis virus (VSV) particle comprising a nucleic acid molecule encoding a viral hemorrhagic fever (VHF) glycoprotein selected from the group consisting of a glycoprotein from Lassa virus; a glycoprotein from Marburg virus; and a glycoprotein from Ebola virus, inserted into the viral genome wherein the foreign glycoprotein has replaced the native VSV glycoprotein and only the VHF glycoprotein is expressed on the surface of the recombinant VSV particle, wherein said recombinant VSV particle is infectious and simulates infection by said VHF virus but does not cause disease or symptoms associated with said VHF.

4. The method according to claim 3 wherein the first gene of the recombinant VSV codes for the VHF glycoprotein.

5. The method according to claim 3 wherein the particle is administered orally.

6. The method according to claim 3 wherein the particle is administered intranasally.

* * * * *